United States Patent [19]

Brown et al.

[11] 4,198,279
[45] Apr. 15, 1980

[54] OXYGEN SENSOR MOUNTING STRUCTURE

[75] Inventors: John T. Brown; Jerry W. Hoskins, both of Corning, N.Y.

[73] Assignee: Corning Glass Works, Corning, N.Y.

[21] Appl. No.: 850,224

[22] Filed: Nov. 10, 1977

[51] Int. Cl.$^2$ ............................................. G01N 27/46
[52] U.S. Cl. .................................................. 204/195 S
[58] Field of Search ............................. 204/1 S, 195 S

[56] References Cited

U.S. PATENT DOCUMENTS

| 3,661,749 | 5/1972 | Richardson | 204/195 S |
|---|---|---|---|
| 3,699,032 | 10/1972 | Rapp | 204/195 S |
| 3,738,341 | 6/1973 | Loos | 204/195 S |
| 3,838,021 | 9/1974 | Arbiter | 204/195 S |
| 3,844,920 | 10/1974 | Burgett et al. | 204/195 S |
| 3,847,778 | 11/1974 | Riddel | 204/195 S |
| 3,864,232 | 2/1975 | Handman et al. | 204/195 S |
| 4,003,814 | 1/1977 | Tarassoff et al. | 204/195 S |
| 4,049,524 | 9/1977 | Togawa et al. | 204/195 S |

Primary Examiner—T. Tung
Attorney, Agent, or Firm—Richard N. Wardell; Clarence R. Patty, Jr.

[57] ABSTRACT

A wall structure is provided for mounting an oxygen sensor probe to accurately measure the oxygen content of flowing elevated temperature atmosphere confined on one side of the wall. The sensor probe is protectively positioned and cushioned within a probe accepting bore through the wall by a flexible fibrous refractory material which thermally insulates and seals the probe within the bore from the surrounding environment. The sensing tip of the probe extends through the wall structure and is exposed to the elevated temperature combustion gases.

8 Claims, 2 Drawing Figures

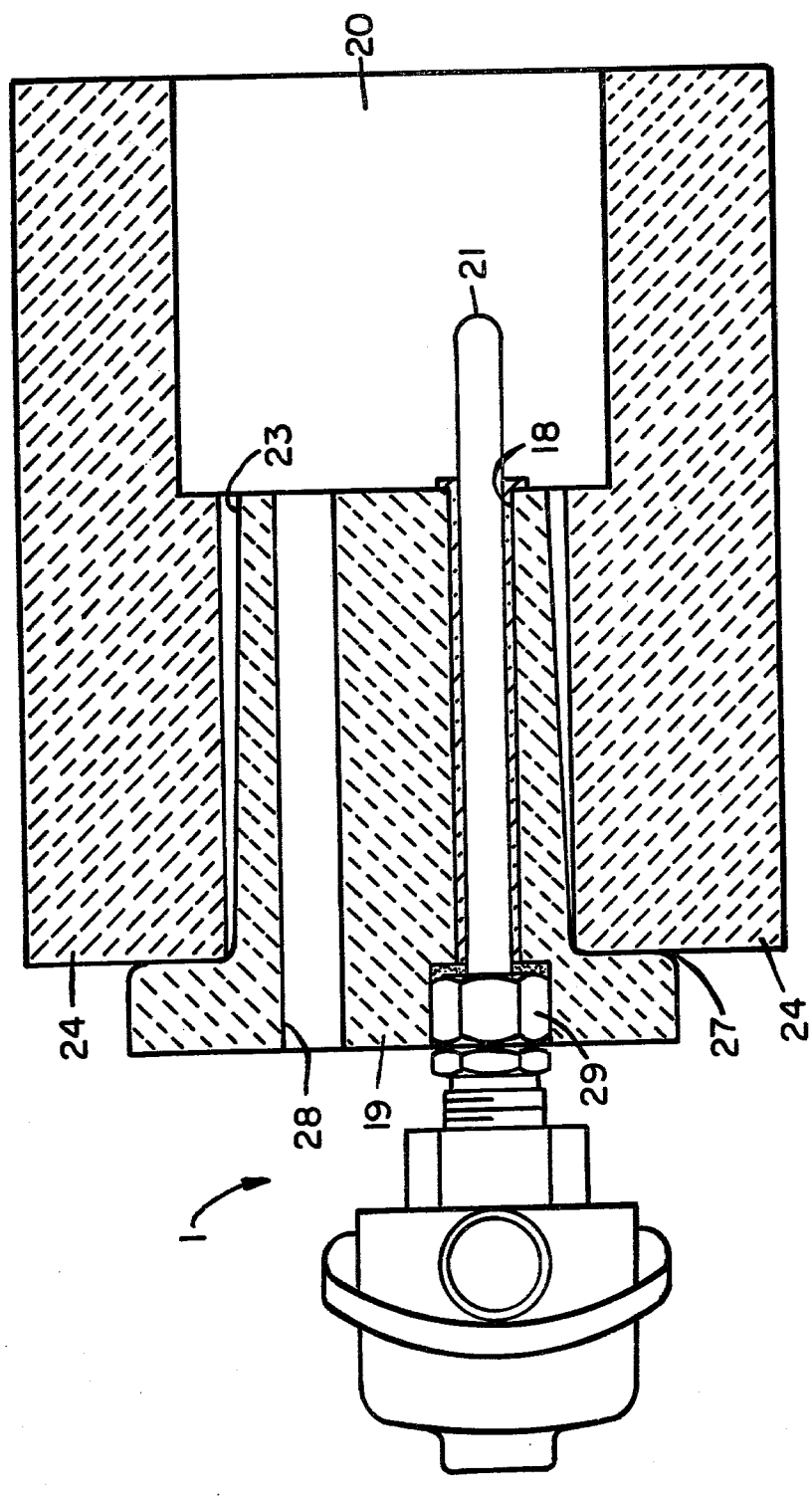

OXYGEN SENSOR MOUNTING STRUCTURE

BACKGROUND OF THE INVENTION

In industrial applications, such as in glass melting furnaces, the ability to continuously and accurately measure the oxygen content of the combustion gases is an invaluable aid in obtaining optimum utilization of fuel. Constant monitoring of the oxygen level also allows for increased stability of a melting process, particularly in glass melting applications where such monitoring can influence the melting rates, fining and refractory corrosion rate, and can ultimately improve glass quality.

Oxygen sensing devices mounted in furnace walls for in situ monitoring of oxygen is known in the prior art. In general these devices have required the elaborate housing of the sensing device to protect it from the furnace environment and from movement, loosening or cracking of the probe. The latter can occur during mounting or as a result of the differing thermal expansion and contractions of the sensing device and its protective casing.

A simple structure for mounting an oxygen sensor probe for in situ monitoring of oxygen levels within a furnace wall has been a difficult problem to solve. This is especially true in glass melting regenerative furnace where there is extensive thermal cycling and the solid electrolyte tube becomes subject to cracking due to thermal shock.

SUMMARY OF THE INVENTION

We have devised a means of protectively mounting an oxygen sensor probe for continuously and accurately monitoring the oxygen content of combustion gases which is of simple design and structure. The invention contemplates replaceably mounting an oxygen sensor probe assembly within a fibrous refractory lined probe-receiving bore of a furnace refractory wall structure.

Briefly stated, the refractory wall structure for replaceably and protectively mounting an oxygen sensor probe to accurately measure the oxygen content of flowing elevated temperature atmosphere on one side of the wall comprises: (1) a wall for confining the elevated temperature on the one side; (2) a probe-receiving bore extending through the wall from the one side or hot side to the other side or cold side; and (3) a flexible fibrous refractory material disposed within the probe receiving bore extending from the hot side to near the cold side of the wall.

The fibrous refractory material forms a lining in contact with the surface defining the bore and serves to seal, cushion and thermally insulate the oxygen sensor probe within the bore.

A preferable mounting structure also comprises a refractory wall structure which includes a replaceable refractory plug containing a probe reclining bore for mounting the oxygen sensor probe in the manner previously indicated. This embodiment of the invention allows the probe to be mounted prior to installation within the furnace wall as a single replaceable unit.

DESCRIPTION OF THE DRAWINGS

FIG. 2 is an illustration of the preferred mounting structure of the oxygen sensor probe.

DESCRIPTION OF EMBODIMENTS

Figure 1:
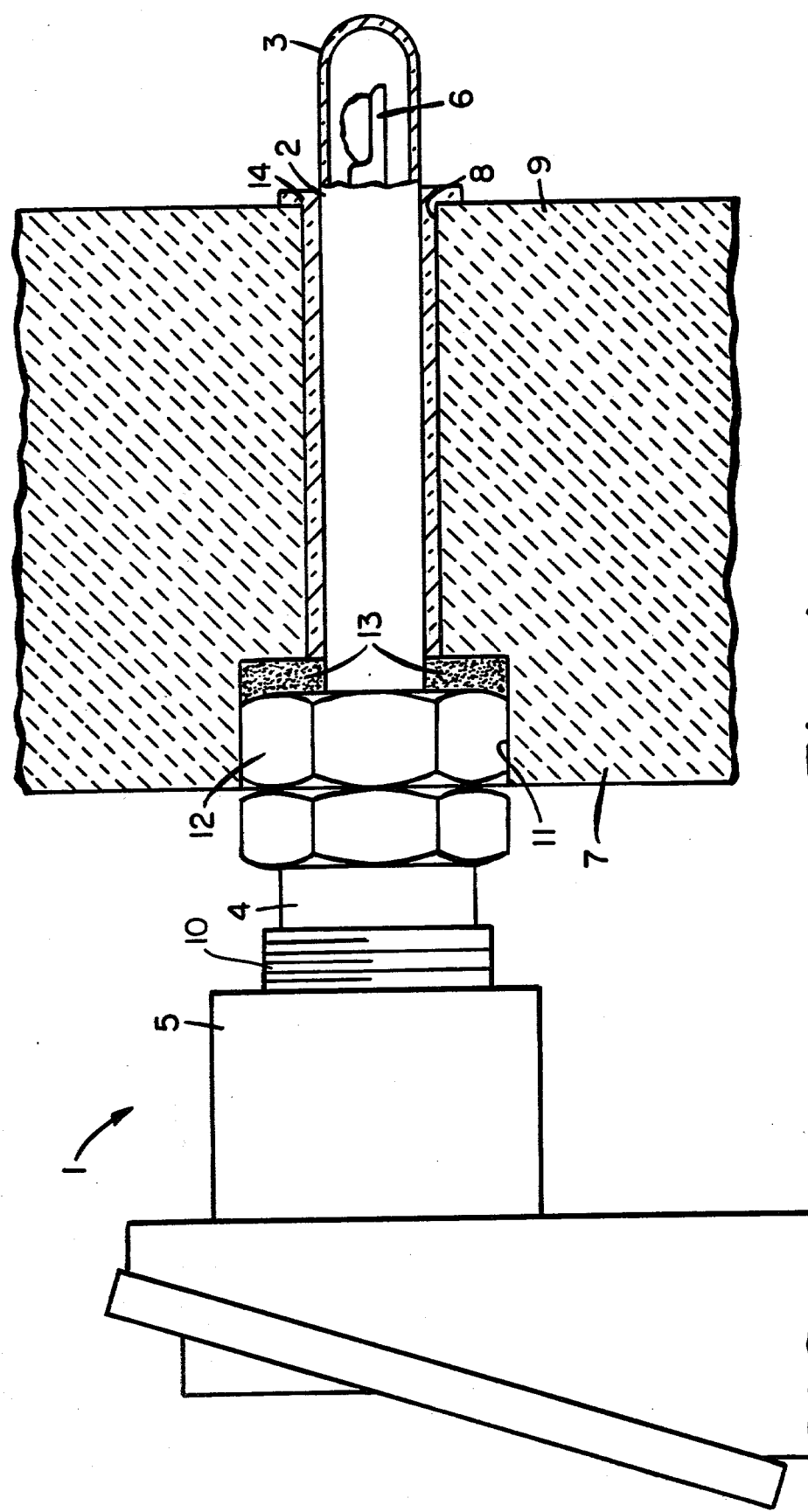
FIG. 1 is a schematic illustration of the mounting structure of the oxygen sensor probe within a wall structure.

FIG. 1 illustrates one embodiment of the mounting structure of an oxygen sensor probe assembly 1 for in situ monitoring of the oxygen contents of combustion gases.

Briefly, the sensor assembly 1 comprises: (a) a solid electrolyte zirconia sensor tube 2, electroded with platinum on its inner and outer surface (not shown), having a closed end or tip 3 and an open end (not shown); (b) a stainless steel bushing 4 having threads on both ends, which is cemented to the open end of the zirconia tube 2; (c) a thermocouple head 5, which is threaded onto one end 10 of the bushing 4, to secure the zirconia tube 2 to the thermocouple head 5, which holds a thermocouple junction (not shown) and (d) a double bore alumina tube 6, which relays the thermocouple wires (not shown) to terminals within the thermocouple head, which also contains the terminals for the sensor electrodes (not shown).

The oxygen sensor probe assembly 1 is mounted within the refractory wall structure 7 having a probe-receiving bore 8 extending therethrough. The wall structure is designed such that one side, the hot side 9, contacts and confines the flowing elevated temperature combustion gases within the furnace wall. The probe-receiving bore 8 extends from the one side (hot side) to the other side (cold side) where it expands to form a small recess 11 designed to accommodate a stainless steel nut 12. The stainless steel nut is cemented 13 within the recess 11 of the bore 8 and serves to rigidly and mechanically hold the probe assembly 1 threadably connected to the nut 12 at the other end of the bushing 4.

In mounting the sensor within the probe-receiving bore 8 of the refractory wall 7, a 1¼″ portion of the sensing tip 3 of the probe assembly is directly exposed to the combustion gases at elevated furnace temperatures.

Disposed within the probe-receiving bore 8 is a flexible, fibrous refractory material 14 which forms a cushioned lining in contact with the wall surface defining the bore and extending the entire length of the bore 8 from the hot side to near the cold side. This fibrous refractory material 14 functions as a thermal insulating barrier and pliable gasket seal which protects the solid electrolyte tube from the high temperature furnace environment.

Any flexible fibrous refractory material which will not flux with the surrounding refractory structure, electrolyte or platinum at high temperatures may be utilized for lining the bore 8. While a pure fibrous sleeving material of woven silica is preferred for economic reasons, zircon or zirconia fibers, either woven or matted, can also be used in this context.

The flexible, fibrous refractory material thermally insulates the solid electrolyte tube 2, within the bore 8, from the high temperatures of the surrounding refractory wall 7 which can cause thermal gradients to develop within the tube and concomitant cracking of the tube due to thermal shock.

Thermal gradients are likely to occur in regenerative, glass melting furnaces immediately after furnace reversals, when the temperature of the wall structure is at its maximum, while the sensor's tip 3 is exposed to the incoming fuel and air at a temperature well below that of the surrounding wall structure.

The fibrous insulating material in these situations, being disposed between the wall of the bore 8 and the solid electrolyte tube 2, prevents the transfer of the heat from the wall to the tube, thereby preventing the development of thermal gradients attributable to the wall instead of conduction along the length of the sensor tube.

The sleeving also acts as a pliable gasket seal protecting the outer platinum electroded surface of the tube, located within the bore 8, from attack by contaminants present in the combustion gases. Contaminants such as lead and antimony and alloy with the platinum within the cooler bore area 8 as a result of condensation within the bore. Such alloying generally results in the forming of a lower melting point composite which, in the high temperature environment of the furnace, subsequently melts and contributes to erroneous sensor readings.

An added advantage of the fibrous material 14 disposed within the probe receiving bore 8 is that is provides a cushion which prevents the solid electrolyte tube 2 from impacting on the refractory wall when the prove assembly is being mounted or removed.

The preferred mounting structure is illustrated in FIG. 2. The oxygen sensor probe 1 is mounted in the same manner as described in FIG. 1, with the exception that it is mounted within a probe-receiving bore 18 of a refractory plug 19 such that the sensor tip 21 is exposed to the flowing elevated temperature combustion gases within a cavity or recess wall area 20. The plug 19 is designed as shown in FIG. 2 with a tapered body 23, which is inserted into a hollow or apertured refractory wall 24, and a head portion 27, designed to project beyond and protrude over one face of the refractory wall to which it can be replaceably and sealably affixed with a sealant such as cement.

As previously described above, the oxygen sensor probe tip 21 is exposed to the combustion gases within a recessed area 20 within the furnace refractory wall. The probe-receiving plug 19, when mounted within the hollow or aperture through the refractory wall 24, extends part way therethrough such that the cavity 20 is formed on one side with the opening between the plug and the hot side of the wall in contact with the elevated temperature combustion atmosphere.

In this embodiment a vent hole 28 within the plug extends from the cavity 20 through to the opposite side of the plug for continuously purging the gases contained within the cavity 20. In such embodiments, where a cavity or recessed area 20 is generated, a minimum positive pressure must exist within the cavity at the sensor location in order to obtain continuous venting of the combustion gases to the outer or opposite wall of the plug. There is, therefore, continuous replacement of the combustion gases around the sensor tip 21. In a mounting structure where the sensor tip is disposed directly within the flowing combustion gases, as in FIG. 1, no such venting is required.

It is evident that both of the embodiments shown for mounting the oxygen sensor probe assembly, viz. FIG. 1 and FIG. 2, may be modified as required to provide for monitoring the oxygen concentration by positioning the probe assembly within a wall structure such that the sensor tip of the probe is directly exposed to the flowing combustion atmosphere (FIG. 1) or exposed within a recessed or cavity area of the furnace wall (FIG. 2).

The preferred embodiment as illustrated in FIG. 2 provides added beneficial means of installing and removing the oxygen sensor probe assembly 1 other than by screwing and unscrewing the sensor from the stainless steel nut 11 of FIG. 1 and at 29 in FIG. 2.

Mounting the oxygen sensor probe assembly 1 within a replaceable plug 19 obviates direct contact with the sensor during its installation and removal since the plug 19 and the probe assembly 1 are capable of being installed and removed as a single unit.

We claim:

1. A furnace wall structure for replaceably and protectively mounting an oxygen sensor probe to accurately measure the oxygen content of flowing elevated temperature combustion gas atmosphere of the furnace on a hot side of the wall, which structure comprises:
   a wall for confining the elevated temperature atmosphere on the hot side thereof,
   a probe-receiving bore extending through the wall from the hot side to a cold side thereof,
   a flexible fibrous refractory material disposed within the probe-receiving bore thereby forming a cushioned lining in contact with the wall surface defining the bore and extending from the hot side to near the cold side for sealing and thermally insulating the probe within the bore, and
   an oxygen sensor probe comprising a solid electrolyte tube with a closed end sensing tip and an outer electroded surface, the probe being replaceably positioned to extend from the cold side to the hot side within the bore and within the cushioned lining with a portion of the sensing tip exposed near the hot side to contact the elevated temperature atmosphere and with the majority of the tube length, including a portion of the outer electroded surface, being sealably cushioned within the lining.

2. The structure of claim 1 including means for replaceably and rigidly holding the probe within the bore.

3. The structure of claim 2 wherein the means for replaceably and rigidly holding the probe within the bore comprises a stainless steel nut cemented into a recess in the cold side froming an expanded part of the bore.

4. The structure of claim 1 including:
   an opening extending through the wall from the hot side to the cold side,
   a plug replaceably and sealably fitted into the opening and extending part way therethrough from the cold side so as to define a cavity in a portion of the opening between the plug and the hot side of the wall, and
   the probe-receiving bore extending through the plug from the cavity to an opposite side of the plug near the cold side.

5. The structure of claim 4 including means for replaceably and rigidly holding the probe within the bore.

6. The structure of claim 5 wherein the means for replaceably and rigidly holding the probe comprises a stainless steel nut cemented into a recess in the opposite side of the plug forming an expanded part of the bore.

7. The structure of claim 4 wherein the plug is a tapered body w'th external surfaces extending between the cavity and the opposite side tapering toward the cavity and engaging the surface of the opening.

8. The structure of claim 1 including
   the wall having a cavity extending from the hot side in contact with the elevated temperature atmosphere part way therethrough and
   the probe-receiving bore extending from the cavity through the wall to the cold side thereof.

* * * * *

UNITED STATES PATENT AND TRADEMARK OFFICE
CERTIFICATE OF CORRECTION

PATENT NO. : 4,198,279

DATED : April 15, 1980

INVENTOR(S) : John T. Brown and Jerry W. Hoskins

It is certified that error appears in the above-identified patent and that said Letters Patent are hereby corrected as shown below:

Column 1, line 59, change "reclining" to -- receiving --.

Column 3, line 12, change "and" to -- can --.

Column 3, line 19, change "is that is" to -- is that it --.

Column 4, in the claims, claim 3, line 39, change "froming" to -- forming --.

Signed and Sealed this

Twenty-second Day of July 1980

[SEAL]

Attest:

Attesting Officer

SIDNEY A. DIAMOND

Commissioner of Patents and Trademarks